United States Patent [19]

Walker

[11] 4,220,446
[45] Sep. 2, 1980

[54] ATTACHABLE TOOTH CLEANING AGENT DISPENSER FOR DENTAL HANDPIECES

[76] Inventor: Donald H. Walker, Box 717 Blue Run Dr., Dunnellon, Fla. 32630

[21] Appl. No.: 966,159

[22] Filed: Nov. 29, 1978

[51] Int. Cl.³ .......................... A61C 1/10; A61C 1/12; A61C 17/02
[52] U.S. Cl. ...................................... 433/85; 433/87; 433/88
[58] Field of Search ....................... 222/389, 327, 334; 32/58, 59, 28; 433/84, 87, 88, 85

[56] References Cited

U.S. PATENT DOCUMENTS

| | | | |
|---|---|---|---|
| 2,697,878 | 12/1954 | Oberley | 32/59 |
| 3,136,456 | 6/1964 | Sherbondy | 322/389 |
| 3,775,849 | 12/1973 | Condon | 32/59 |

Primary Examiner—Robert Peshock
Attorney, Agent, or Firm—Mason, Fenwick & Lawrence

[57] ABSTRACT

An attachable cleaning agent dispenser for retrofit use in combination with a conventional dental handpiece including a frame, gripping members for removably attaching the frame to a dental handpiece, a reservoir for containing a cleaning agent with the reservoir mounted on the frame, a dispensing orifice mountable adjacent a cleaning tool on the dental handpiece, a cleaning agent flow passageway connecting the reservoir and the orifice, a pneumatic piston slidable within the reservoir for ejecting cleaning agent from the reservoir, into the passageway, and out the orifice when pneumatic pressure is applied to the piston by finger control by an operator of the handpiece.

8 Claims, 4 Drawing Figures

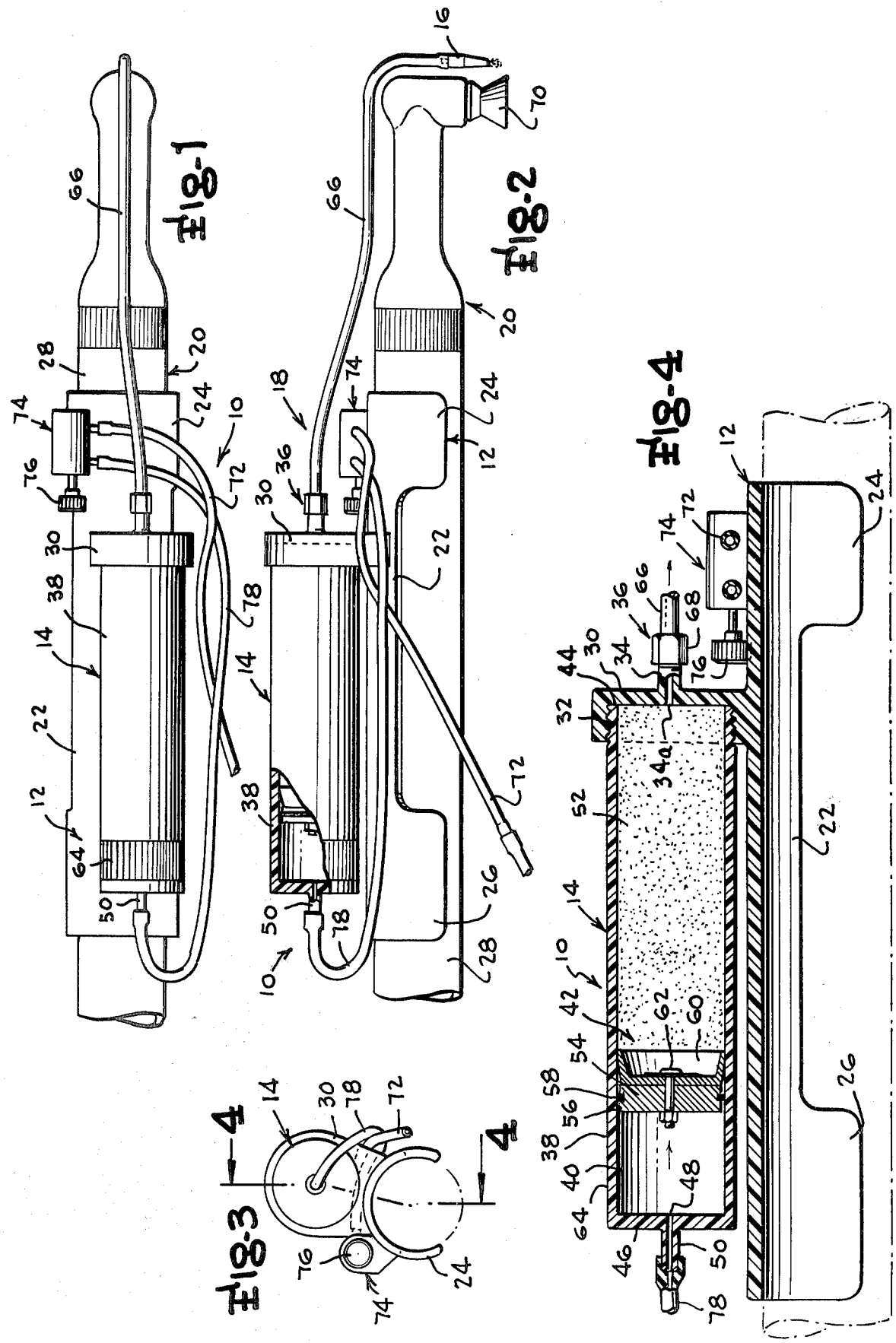

ATTACHABLE TOOTH CLEANING AGENT DISPENSER FOR DENTAL HANDPIECES

BACKGROUND AND OBJECTS OF THE INVENTION

This invention is in the field of dispensers and is specifically directed to the field of dental teeth cleaning apparatus.

Prior known dental handpiece cleaning apparatus including a cleaning agent dispensing device have generally been foot operated which has prevented acceptance of these devices due to the inherent complexity of operating two separate foot pedals since one is required for the dental handpiece.

Additionally, prior known dental teeth cleaning apparatus such as disclosed in U.S. Pat. Nos. 3,987,550 and 3,977,084, have provided cleaning agents to the working tool of the dental handpiece from reservoirs which are integrally formed in the handpiece. These previously known cleaning agent dispensing devices have required either an additional dental handpiece or the replacement of the handpiece utilized by the dentist or dental technician. In each case, the passageway for the cleaning agent passes through the center of the cleaning cup and adjacent supporting and rotating portions of the handpiece requiring a specially constructed handpiece and attachments not suitable for existing dental apparatus. These previously known devices have been large and cumbersome which has decreased the efficiency and increased the fatigue of the operator.

Therefore, it is the object of the present invention to provide a novel attachable tooth cleaning agent dispenser for retrofit on a conventional dental handpiece.

Another object of the present invention is to provide a hand controlled, pneumatically operated and attachable tooth cleaning agent dispenser for selectively controlling the supply of dental material delivered to the applicator cup on a dental handpiece.

A further object of the present invention is to provide a novel attachable tooth cleaning agent dispenser which is economical to manufacture and easy to operate.

A still further object of the present invention is to provide a novel attachable tooth cleaning agent dispenser which can be quickly and easily attached and removed from a conventional dental handpiece.

Obtainment of the objects of this invention is enabled through the provision of a dispenser including a frame having opposed resilient gripping members for engaging a portion of an enlarged section on a conventional dental handpiece with a reservoir for containing a tooth cleaning agent supported on the attachable frame. The reservoir includes a cylinder in which a piston is actuated by pressurized air supplied through an operator controlled valve with an opposite side of the piston engaging the cleaning agent and forcing it through a flow passageway to an orifice positionable adjacent the tooth cleaning tool mounted in the dental handpiece. This dispenser permits the dentist or dental technician to effect hand or finger control the rate of flow of cleaning agent applied to the cleaning tool as necessary during the cleaning and polishing of the patient's teeth. The reservoir may be opened to permit the addition of cleaning agent to the reservoir when it has been emptied.

A better understanding of the manner in which the preferred embodiment of the invention achieves the objects of the invention will be enabled when the following written description is read in conjunction with the appended drawings.

BRIEF DESCRIPTION OF THE FIGURES

FIG. 1 is a top elevational view of the preferred embodiment mounted on a conventional dental handpiece;

FIG. 2 is a side elevational view of the preferred embodiment shown in FIG. 1;

FIG. 3 is a rear elevational view of the preferred embodiment; and

FIG. 4 is a fragmentary cross-sectional view taken along lines 4—4 in FIG. 3.

DETAILED DESCRIPTION OF A PREFERRED EMBODIMENT

Attention is initially invited to the various figures of the drawings illustrating the preferred embodiment of the invention generally indicated by reference numeral 10, which includes a frame 12, a reservoir 14, a dispensing nozzle 16 and a pneumatic pressure supply assembly 18. The preferred embodiment is shown mounted on a conventional dental handpiece 20.

The frame 12 includes a semi-cylindrical base 22 formed of injection molded plastic or the like and having a forward saddle formation formed of a pair of downwardly extending gripping portions 24 and a rear saddle formation formed of a rear pair of downwardly extending gripping portions 26. The downwardly extending gripping portions 24 and 26 form concave arcuate saddle-like areas with the base 22 which are generally semi-cylindrical and extend cross-sectionally for more than half a circle to project inwardly. This configuration causes the lower portions to extend around the cylindrical handle portion 26 of the dental handpiece 20, as shown particularly in FIG. 3, to retain the dispenser 10 in the desired position on the dental handpiece 20. Extending upwardly from the base 22 and integrally formed therewith is a reservoir support bracket 30 having a rearwardly opening threaded bore 32 and an outlet nipple 34, and a flow passageway 34a communicating the threaded bore 32 with a tubing coupler assembly 36 mounted on the forward outlet nipple 34.

The reservoir 14 includes a cylindrical housing 38 having a cylindrical inner surface 40 to receive a free piston assembly 42 to be described hereafter. The forward open end of the reservoir 14 includes a threaded portion 44 which is engageable with the threaded bore 32 on the support bracket 30 as shown in FIG. 4. The end of the reservoir 14 opposite the threaded portion 44 is closed by an end wall 46 having a passageway 48 extending therethrough and into an integrally formed tubular inlet nipple section 50 to permit the application of pneumatic pressure to the piston assembly 42.

A fluid tooth cleaning agent 52 is contained within the reservoir 14 and is expelled therefrom by the piston assembly 42 which includes a base disc 54 having an annular groove 56 extending around the perimeter of the disc to receive an O-ring 58 which seals against the inner cylindrical surface of the reservoir housing 38 and prevents contact between the disc 54 and the housing. A forwardly opening cup seal 60 is retained on the base disc 54 by a bolt and nut assembly 62 which extends through the center of the cup seal 60 and the base disc 54 to fasten the cup seal to the forward face of the base disc 54. The cup seal 60 flares outwardly to contact the inner cylindrical surface of the housing 38 and provide a tight seal therebetween. A textured surface area 64 may be added on the outer surface of the rear of the housing 38 to provide a more positive grip for the operator who is removing or assemblying the reservoir housing 38 to the support bracket 30.

The dispensing nozzle 16 is connected to the flow passageway 34 in the support bracket 30 by a flow tube 66 connected at one end to the nozzle 16 and at the opposite end to the coupler assembly 36 which locks the flow tube 66 in the desired position in communication with the outlet nipple 34 and passageway 34a from the reservoir. The flow tube 66 may be formed of a rigid plastic or any other desired material such as stainless steel or aluminum. The coupler assembly 36 is of conventional configuration having a locking nut 68 which engages a threaded portion on the nipple 34 projecting from the upright support bracket 30. The dispensing nozzle 16 directs the cleaning agent 52 to a position adjacent the working tool or dentifrice cup 70 on the dental handpiece 20.

Pressurized air is supplied to the dispenser by a supply air line 72 which provides pressurized air from a conventional supply such as a pump which is not shown. The flow of air through the supply line 72 is controlled by a conventional shutoff valve 74 which is mounted on a forward portion of the base 22. The shutoff valve 74 is normally closed thereby preventing the flow of air into the reservoir until desired by the operator. A pushbutton 76 on the rear of the valve 74 is pushed forward by the finger of the operator when desired to open the valve and direct pressurized air from the supply line 72 to an inlet line 78 which is connected from the valve 74 to the inlet tube 50 on the rear of the reservoir 14 as shown in the various figures.

Operation of the cleaning agent discussed herein according to the present invention is easily and quickly accomplished by the dentist or dental technician. The frame 12 is clamped onto the dentist handpiece 20 by pressing the forward and rear downwardly projecting portions 24 and 26 over the handle portion 28 of the handpiece as shown in the various figures. The pressurized air supply line 72 is connected to the supply source and the operator presses the pushbutton 76 on the control valve 74 to direct pressurized air to the back side of the base disc 54 which causes the piston assembly 42 to move forward creating pressure in the cleaning agent 52 and causing it to flow through the flow tube 66 and out the nozzle 16, as shown in FIG. 2, adjacent the cleaning tool 70 for application to the teeth of the patient. The control valve 74 is operated to achieve the desired flow rate of cleaning agent to the teeth. If no cleaning agent is desired, the operator simply lets the pushbutton 76 move rearwardly to its normal position as shown in the figures.

When additional cleaning agent must be added to the reservoir 14, the operator grasps the gripping area 64 and rotates the reservoir to disengage the threaded bore 32 from the threaded portion 44 on the reservoir. The piston assembly 42 may then be forced rearwardly to the end wall 46 of the reservoir and additional cleaning agent added to the reservoir after which the reservoir may be reassembled by appropriately engaging the threaded portion 44 with the threaded bore 32 on the support bracket 30. The dispenser is then ready for use as previously described.

The present invention permits the application of a cleaning agent to the teeth while reducing the time-consuming and inconvenient practice of picking up the materials from a supply receptacle, without requiring any modification when used with a conventional headpiece.

From the foregoing detailed description, it will be evident that there are a number of changes, adaptations and modifications of the present invention which come within the province of those skilled in the art. However, it is intended that all such variations not departing from the spirit of the invention, be considered as within the scope thereof as limited solely by the appended claims.

I claim:

1. A removably attachable tooth cleaning agent dispenser for use as a retrofit attachment on a conventional dental handpiece, said dispenser comprising a frame, gripping means for removably attaching said frame to a dental handpiece laterally abutting a handle portion thereof, a reservoir for containing said cleaning agent, means mounting said reservoir on said frame, a dispensing nozzle mountable adjacent a cleaning tool on said dental handpiece, a cleaning agent flow passageway connecting said reservoir and said nozzle, and pneumatic means including a finger operated control valve adjacent said handle portion at a location normally adjacent a finger of the operator when holding the dental handpiece during use and pneumatically movable means responsive to said valve operatively connected with said reservoir for ejecting a cleaning agent from said reservoir into said passageway, and out said nozzle when desired by an operator of said handpiece.

2. The removably attachable dispenser of claim 1 wherein said reservoir has a cylindrical inner surface and wherein said pneumatic means includes a piston slidable in said reservoir on said cylindrical inner surface, a pneumatic supply line communicating with one side of said piston and the opposite side of said piston communicating with said cleaning agent flow passageway, and said control valve being located in said pneumatic supply line immediately adjacent said opposite side thereby permitting control of the rate of flow of cleaning agent from the dispensing nozzle by an operator of the dispenser.

3. The removably attachable dispenser of claim 2, wherein said control valve includes a valve housing laterally adjacent said opposite side of said piston having a push button valve therein including a valve actuator member having a push button head to be engaged by the operator's finger and moved along an axis paralleling the handle portion of the dental handpiece between open and closed positions.

4. The removably attachable dispenser of claim 2 wherein said reservoir has a threaded outer portion and said frame has a threaded bore to threadingly receive the threaded outer portion of said reservoir thereby permitting removal and refilling of the reservoir as desired.

5. The removably attachable dispenser of claim 1 wherein said frame comprises a cylindrically concave elongated base portion shaped to conform to and fit against the handle portion of the dental handpiece having integrally formed at opposite ends thereof said gripping means comprising opposed resilient saddle shaped cylindrically concave gripping members of slightly greater than half-circular cross-sectional circumferential extent for engaging a portion of a cylindrical section on the dental handpiece.

6. The removably attachable dispenser of claim 2 wherein said frame comprises a cylindrically concave elongated base portion shaped to conform to and fit against the handle portion of the dental handpiece having integrally formed at opposite ends thereof said gripping means comprising opposed resilient saddle shaped cylindrically concave gripping members of slightly greater than half-circular cross-sectional circumferential extent for engaging a portion of a cylindrical section on the dental handpiece.

7. The removably attachable dispenser of claim 3 wherein said frame comprises a cylindrically concave elongated base portion shaped to conform to and fit against the handle portion of the dental handpiece having integrally formed at opposite ends thereof said gripping means comprising opposed resilient saddle shaped cylindrically concave gripping members of slightly greater than half-circular cross-sectional circumferential extent for engaging a portion of a cylindrical section on the dental handpiece.

8. The removably attachable dispenser of claim 4 wherein said frame comprises a cylindrically concave elongated base portion shaped to conform to and fit against the handle portion of the dental handpiece having integrally formed at opposite ends thereof said gripping means comprising opposed resilient saddle shaped cylindrically concave gripping members of slightly greater than half-circular cross-sectional circumferential extent for engaging a portion of a cylindrical section on the dental handpiece.

* * * * *